(12) United States Patent
Desarzens (10) Patent No.: US 7,115,119 B2
(45) Date of Patent: Oct. 3, 2006

(54) DUAL REAMER HOLDER FOR SURGICAL USE

(75) Inventor: Yves Desarzens, Corgémont (CH)

(73) Assignee: Precimed S.A., Orvin (CH)

(*) Notice: Subject to any disclaimer, the term of this patent is extended or adjusted under 35 U.S.C. 154(b) by 192 days.

(21) Appl. No.: 10/441,148

(22) Filed: May 19, 2003

(65) Prior Publication Data

US 2003/0216716 A1   Nov. 20, 2003

Related U.S. Application Data

(63) Continuation-in-part of application No. 10/429,897, filed on May 5, 2003, which is a continuation-in-part of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(51) Int. Cl.
    *A61B 17/00* (2006.01)

(52) U.S. Cl. .......................................... 606/1; 606/80
(58) Field of Classification Search .................. 606/1, 606/79–81
    See application file for complete search history.

(56) References Cited

U.S. PATENT DOCUMENTS

| | | | | |
|---|---|---|---|---|
| 4,834,092 A | * | 5/1989 | Alexson et al. ................. | 606/1 |
| 5,499,985 A | * | 3/1996 | Hein et al. ..................... | 606/99 |
| 6,206,872 B1 | * | 3/2001 | Lafond et al. .................. | 606/1 |
| 6,450,948 B1 | * | 9/2002 | Matsuura et al. ........... | 600/139 |

* cited by examiner

*Primary Examiner*—Michael Peffley
*Assistant Examiner*—Pete Vrettakos
(74) *Attorney, Agent, or Firm*—Moetteli & Associés SàRL; John Moetteli (57) ABSTRACT

A surgical tool holder has a shank having a central axis, a first driveable end and second coupling end. The second end has a coupling device having interfaces each for mating with corresponding structures on the inside of a hollow reamer. The interfaces mate with centering structures at or near a base end of each tool, the tool being held in functional assembly to the shank by a releasable locking mechanism.

11 Claims, 6 Drawing Sheets

DUAL REAMER HOLDER FOR SURGICAL USE

"This application is a continuation-in-part of U.S. patent application Ser. No. 10/429,897, entitled Hand-Held Instrument Holder for Surgical Use, filed on May 5, 2003, this in turn being a continuation-in-part of U.S. patent application Ser. No. 10/391,464, which is now U.S. Pat. No. 7,056,317, entitled Instrument Holder for a Surgical Instrument, filed on Mar. 18, 2003, which is in turn continuation of Ser. No. 09/902,369, which is now U.S. Pat. No. 6,540,739, filed on Jul. 9, 2001, which in turn is a continuation of Ser. No. 09/602,341 filed Jun. 24, 2000 and now U.S. Pat. No. 6,264,647 issued Jul. 24, 2001, the contents of which are incorporated herein by reference thereto."

BACKGROUND OF THE INVENTION

This invention relates to surgical tool holders, and more particularly, to holders of rotary surgical cutting tools.

Surgical tools and their respective holders have to be kept clean and sterile before any use in a hospital environment in order to minimize risk of transfer of disease or infection from patient to patient following the emergence of certain "prions" that are not killed by normal hospital sterilization and thus need to be physically removed through washing and rinsing. A surgical tool, for example for preparing for the fitting of a hip prosthesis, works in a medium which causes considerable soiling of the tool and of the tool holder. Despite the importance of doing so, the thorough cleaning of these devices is difficult. Surgical tool holders of the prior art are designed such that washing and rinsing are generally not an effective way of cleaning the tool. This is due to the small spaces left between component parts which allow only minimal access by cleaning agents.

Further, among the many different styles of reamers used by surgeons in orthopaedic surgical operations, there are two that are particularly pervasive, yet which present different interfaces to the holders, thus not permitting a single reamer holder to be able to fasten to the two different interfaces. This requires that the two reamers each have a dedicated holder, which adds to the bulk and expense of surgical tool kits.

What is needed therefore is a surgical tool holder which is quickly and simply disassembled for cleaning and sterilization. Still further, what is needed is a dual reamer holder capable of holding the two different styles of reamers which are pervasively used in orthopaedic surgery.

The surgical tool holder of the invention has a shank having first driveable end and second coupling end, a coupling device mounted on the coupling end, and a locking mechanism. The coupling device has at least two pairs of bayonet interfaces spaced apart from the central axis. Each interface is made up of at least a portion of a slot having a two-tiered opening transverse to the central axis. The two-tiered opening is of a form so as to be able to receive corresponding elongated structures of at least two types of reamer tools, at the selection of the user. The corresponding structures are elongated in a direction substantially perpendicular to the central axis.

In another aspect of the invention, the locking mechanism in made up of an annular capture component, a spring, a locking sleeve which slides on the shank, and a locking device. The capture component is mounted so as to slide along the shank and includes two pairs of longitudinally protruding pins, the matching pin to the pair being positioned 180 degrees apart. In a preferred configuration, the four pins are spaced apart evening on a circle centered on the axis of the shank.

The locking device cooperates with the capture component so as to lock the tool onto the interface. The spring biases the capture component in a locking direction and bears on the locking sleeve. The locking sleeve is disengageably lockable to the shank via a connection device. The connection device is preferably a bayonet mechanism.

The object of the invention is to enable quick disassembly for cleaning and component sterilization.

Another object of the invention is to provide one holder capable of holding the two pervasively used hollow reamers.

BRIEF DESCRIPTION OF THE DRAWINGS

The attached drawings show embodiments of the invention by way of example.

DETAILED DESCRIPTION OF THE PREFERRED EMBODIMENT(S)

Figure 1:
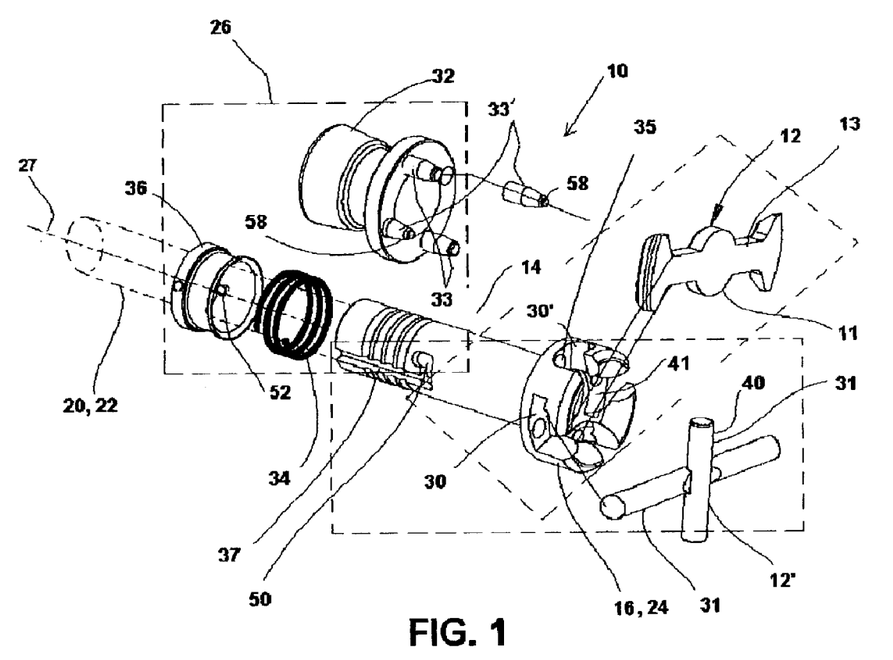
FIG. 1 is an exploded view of the tool holder of the invention, adjacent tools to which the holder interfaces.

Referring now to FIG. 1, the dual surgical reamer holder 10 of the invention is shown. The holder 10 connects to a surgical tool 12 or 12' to enable controlled manipulation of that tool. The holder 10 has a shank 14 having a coupling end 16, a drive interface 20 attached to an opposite end 22 (shown in phantom lines) of the shank, a coupling device 24 and a locking mechanism 26. The coupling end 16 has a series of bayonet grooves 30 therein, cut transverse to the central axis 27 of the shank 14, and having a two-tiered form in that there are two surfaces presented for receiving an elongated cross bar 31, 53 of an OTHY™-type or PRECIMED™-type of reamer tool 12 or 12'. The locking mechanism 26 is made up of a capture sleeve 32, a helical compression spring 34, a locking sleeve 36 all of which slide along the shank 14, and pin receiving holes 35. Preferably, to ensure that the tool 12' is retained in an axially aligned relationship with the holder 10, a central recess 41 capable of receiving a boss 11 on the tool 12' is centrally disposed in the coupling end 16 of the shank 14.

The annular capture sleeve 32 mounts so as to slide along the shank 14. Pins 33 are mounted in the capture sleeve 32 and enter into the corresponding holes 35 in the coupling end 16, thus preventing relative rotation of the sleeve 32 with respect to the shank 14.

Tool 12 has centering bars 40, also known as cross bars 31, which are received into recesses 55 in the capture sleeve 32, and then locked into the recesses when the capture sleeve is biased up the shank into a locked position, thus ensuring that the cross bar is locked into the bayonet groove 30. Note that each groove 30 has a recess 53 in order to capture cross bars 31. The spring 34 biases the capture sleeve 32 in a locking direction, bearing against the locking sleeve 36. The locking sleeve 36 is disengageably lockable to the coupling end 16 of the shank 14 via a bayonet mechanism, which includes a bayonet slot 50 and a locking pin 52. The bayonet slot 50 is cut in the coupling end 16 of the shank 14. The locking pin 52 is press fit into the locking sleeve 36.

The locking sleeve 36 locks over the shank 14 near the coupling end 16. The shank 14 has a longitudinal groove 37 within which the bayonet pin 52 slides so as to enable the locking pins 52 or 52' to freely slide along the shank 14 when the locking sleeve is unlocked and slid back along the shank, in order to provide cleaning access to all surfaces of the locking mechanism 26.

Figure 2:
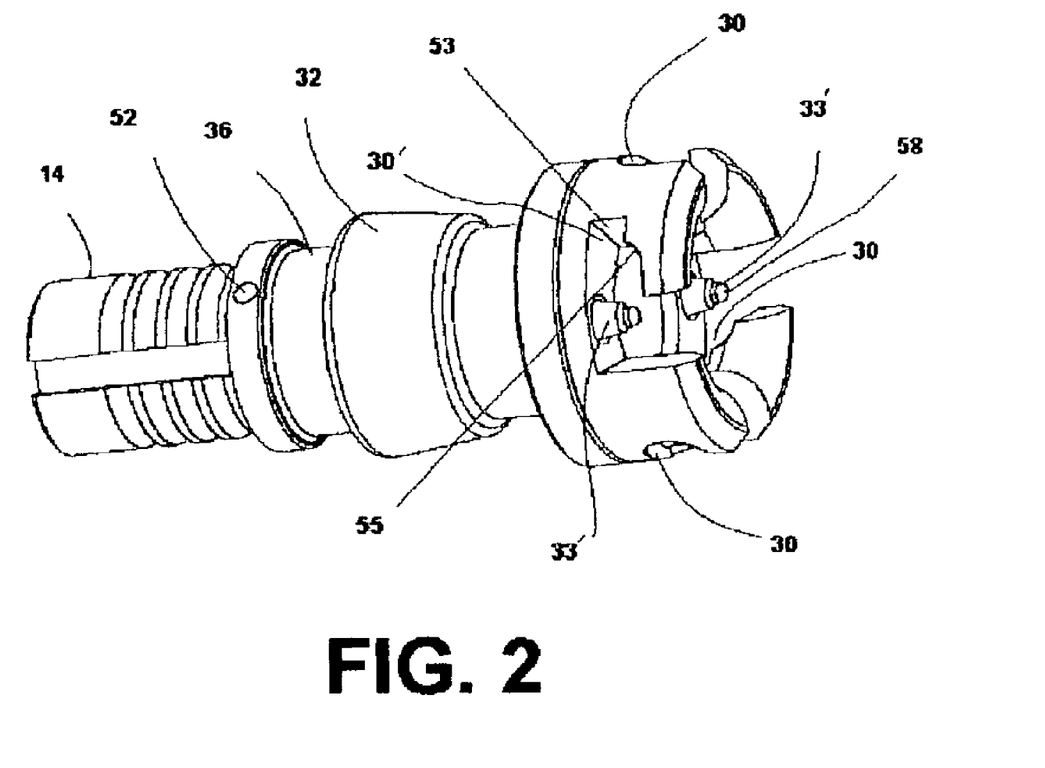
FIG. 2 is an assembled, perspective view of a tool holder of the invention.
Figure 3:
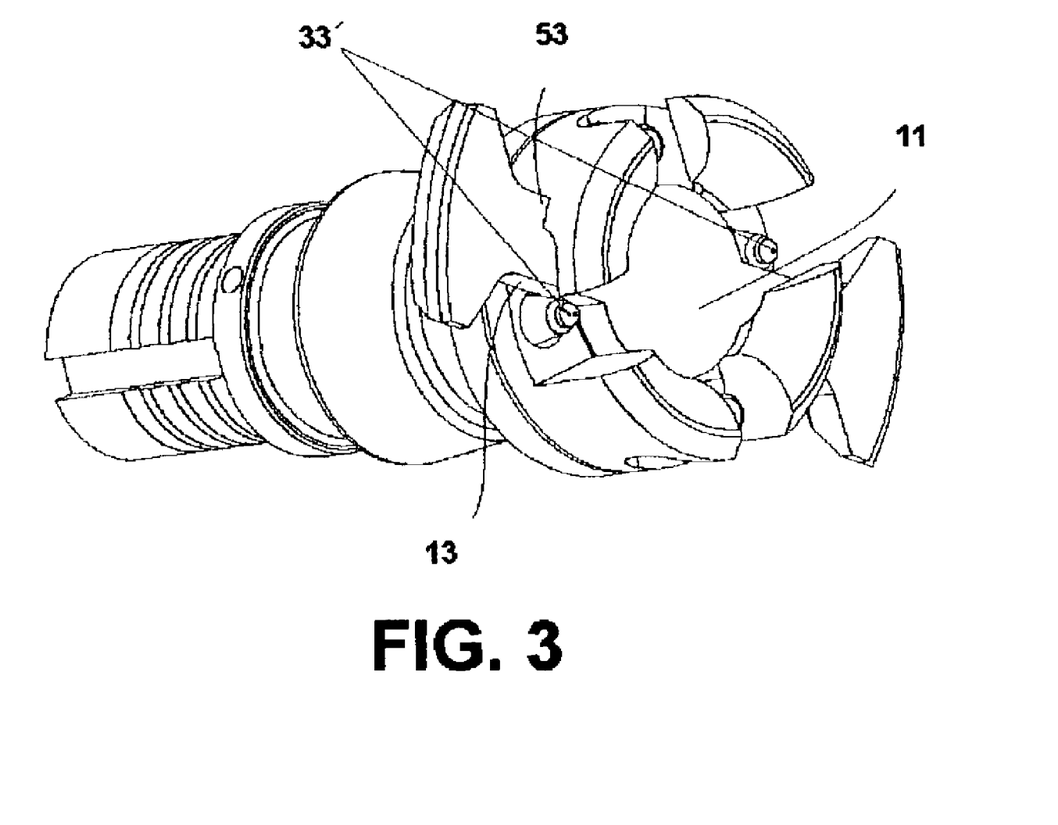
FIG. 3 is a perspective view of the tool holder of the invention holding an "OTHY"™-type tool.
Figure 4:
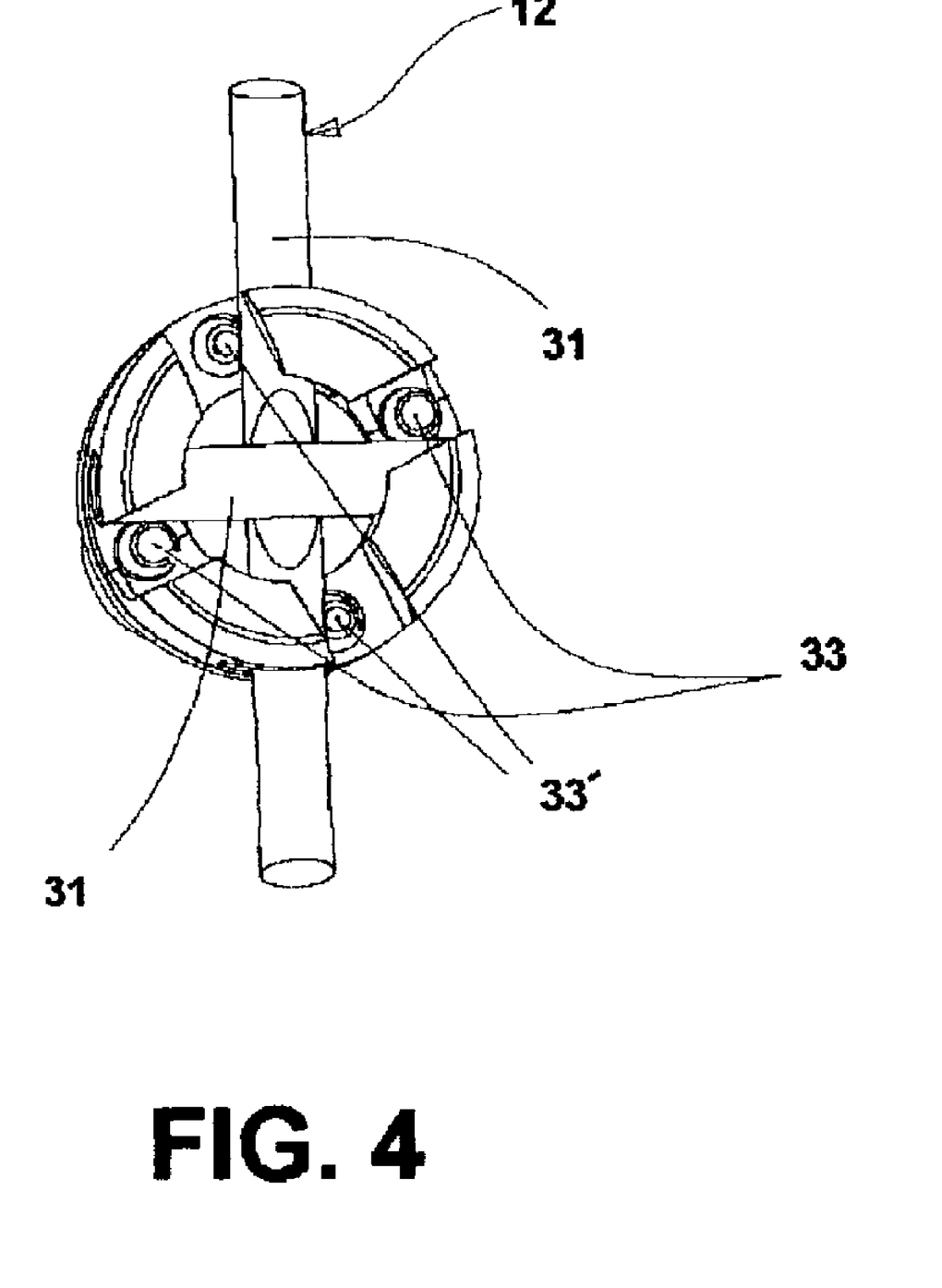
FIG. 4 is a perspective view of the tool holder of the invention holding a "PRECIMED"™-type tool.

Referring now to FIG. 2, all recesses 30 receive the cross bar 31 of the PRECIMED™ tool 12 (shown in FIG. 4) and specialized recesses 30' receive the boss 11 and rectangular arm 13 (shown in FIG. 3) of the OTHY™ reamer 12'. Note that the recesses 30' include a narrow rectangular arm receiving portion 53. Further, pins 52' include small nipples 58 on their ends, which enable the pins to lock in the cross bars 31 more fully, while rising along the shank 14 to the same position (approximately) as is the case when the arms 13 of the "OTHY" product are captured, thus ensuring that the visual impression of locking is consistent when locking either product into the holder 10, despite the different geometric configuration of the interfaces. Thus, the current embodiment requires that the user place the arm 13 of the "OTHY"™-type tool in the appropriate corresponding recesses 30'.

The pins 33 and 33' are chamfered or tapered in order to wedge the rectangular arm 13 or the bar 31 into the corresponding recesses 53 or 55 respectively, so as to eliminate play.

Figure 5:
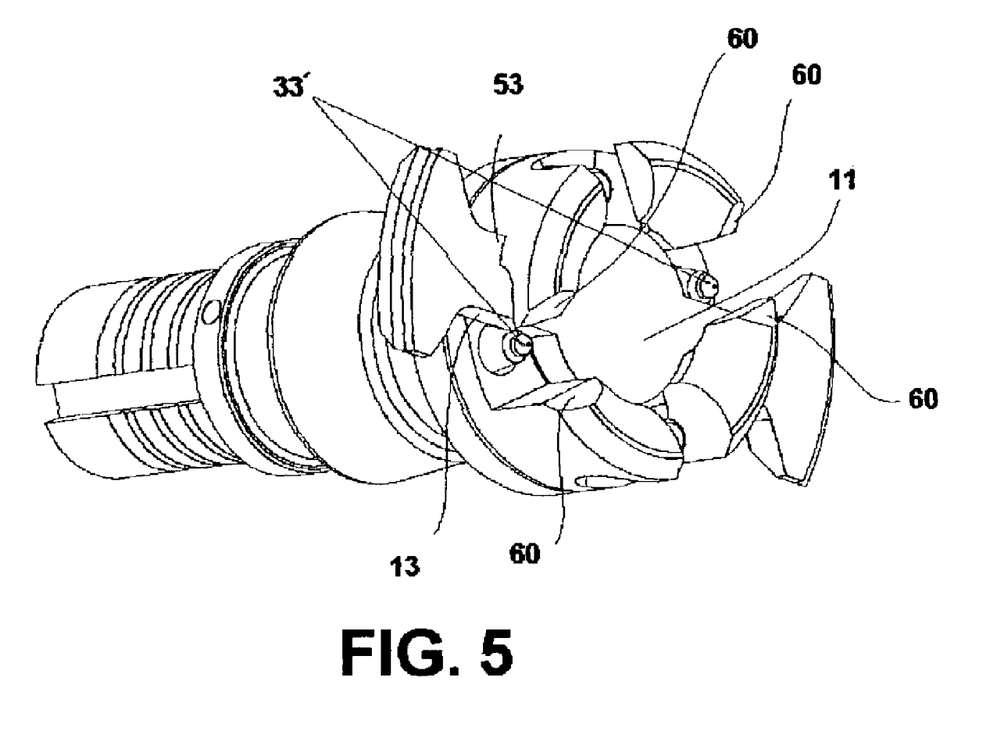
FIG. 5 is a perspective view of the tool holder of the invention, showing a lead-in chamfer to facilitate the insertion of a tool.

Referring now to FIG. 5, optionally, chamfered surfaces 60 facilitate the insertion of the rectangular arm 13 or the bar 31 into the corresponding recesses 30 or 30'.

Figure 6:
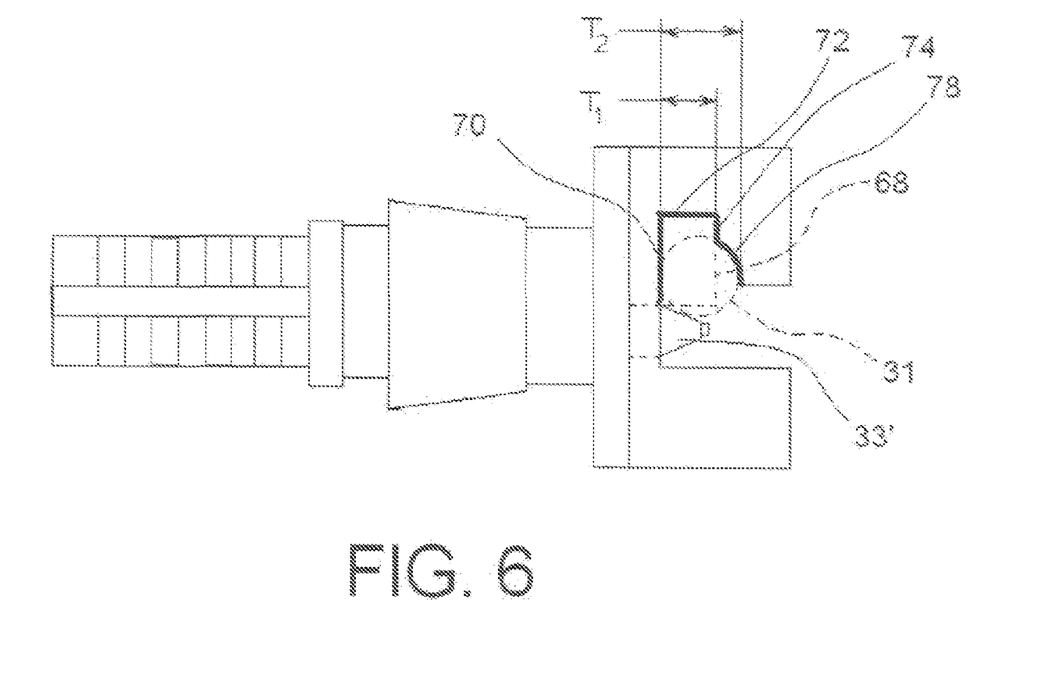
FIG. 6 is a side view of the tool holder of the invention.

Referring now to FIG. 6, it can be clearly seen (see also FIG. 2) that grooves 30 have recess 53, these recess each have a two-tiered structure. A first tier $T_1$ of the opening which the groove 30 defines accommodates the rectangular cross section 68 "OTHY"™-type reamer (see FIG. 5), capturing the rectangular cross section 68 (shown in dashed lines in the figure) against three surfaces 70, 72, and the locking pin 33'. A second tier $T_2$, captures and locks a round bar 31 (shown in dashed lines in the figure) of the "PRECIMED"™ cross bar reamer interface against rounded surface 78 and the pin 33'.

In operation, the cross bar 31 or the bar 13 enters the appropriate bayonet groove 30 or 30' and is turned so as to move into the recess 55 or the receiving portion 53, as the case may be. The tool 12 or 12' is locked in this position when the capture sleeve 32 is raised into a position in which the pins 33 and 33' pass through the holes 35 and into recesses 30 and 30' of the holder 10 so as to lock the tool in place inside the recess.

To unlock the holder 10, the locking sleeve 36 is urged against the bias of spring 34 so as to lift it out of a bayonet seat 51, and then twisted so as to move the pin 52 out of the bayonet slot 50 in the coupling end 16 of the shank 14. The locking sleeve 36 may then be slid back along the shank 14, releasing the spring 34 and the sleeve 32, and thereby providing cleaning and sterilization access to the recesses that might otherwise not be accessible.

In an advantage of the invention, the bayonet mechanism holds the locking sleeve 36 and thus the spring 34 in an operational position, as well as enabling quick disassembly for cleaning and component sterilization.

In another advantage of the invention, the holder is adapted to hold more than one tool interface, thus minimizing the bulk and weight of a surgeon's tool kit.

In another advantage, the holder 10 of the invention minimizes play and maximizes alignment with the turning axis 27.

Although illustrative embodiments of the invention have been shown and described, a wide range of modification, change and substitution is contemplated in the foregoing disclosure and in some instances, some features of the present invention may be employed without a corresponding use of the other features. The elastic devices used of course can be selected from a large variety of equivalents to a helical, compression spring, including, for example, leaf springs, flat springs, multiple compression springs, just to name a few. Still further, the connection mechanism can be substituted for a variety of connection mechanisms such as a threaded connection mechanism, a clasp, spring detents, or even magnetic retention devices. Accordingly it is appropriate that the appended claims be construed broadly and in a manner consistent with the scope of the invention.

What is claimed is:

1. A surgical tool holder comprising a shank having a central axis, a first driveable end and second coupling end, the second end comprising a coupling device which couples to a corresponding structure of a reamer tool and holds such tool in functional assembly to the shank by a releasable locking mechanism, the holder characterized by the fact that the coupling device has at least two pairs of bayonet interfaces spaced apart from the central axis, each interface comprising at least a portion of a slot having a two-tiered opening transverse to the central axis of a form so as to be able to receive corresponding elongated structures of at least two types of reamer tools, at the selection of the user, the corresponding structures being elongated in a direction substantially perpendicular to the central axis.

2. The surgical tool holder of claim 1, wherein the releasable locking mechanism comprising a locking sleeve slideably disposed about the shank, a spring biased against a capture sleeve by the locking sleeve, and a connection device retaining the locking sleeve in a fixed position during use, whereupon release of the connection device enables quick disassembly of the locking sleeve, spring and capture sleeve for cleaning and component sterilization.

3. The surgical tool holder of claim 1, wherein the coupling device comprises a capture sleeve against which the spring is biased by the locking sleeve, the capture sleeve being longitudinally slideable along the shank, constrained to rotate with the shank and presenting longitudinally protruding pin pairs, each pair being disposed about a circle centered on the axis of the shank and capable of passing through openings in the coupling end of the shank and the into holder recesses so as to block a selected reamer tool in the corresponding holder recesses.

4. The surgical tool holder of claim 1, wherein a handle is attached to the driveable end of the shank.

5. The surgical tool holder of claim 3, wherein when the locking sleeve is unlocked and slide back tug the shank, cleaning access to all surfaces of the locking mechanism is facilitated.

6. The surgical tool holder of claim 1, wherein a first interface mates with a cross bar reamer interface.

7. The surgical tool holder of claim 1, wherein a second interface mates with a bar boss reamer interface.

8. The surgical tool holder of claim 1, wherein the spring is a helical compression spring.

9. The surgical tool holder of claim 1, wherein the connection device is a bayonet mechanism.

10. The surgical tool holder of claim 9, wherein the bayonet mechanism is comprised of a bayonet slot and a locking pin.

11. The surgical tool holder of the claim 10, wherein the bayonet slot is disposed on he shank.

* * * * *

UNITED STATES PATENT AND TRADEMARK OFFICE
CERTIFICATE OF CORRECTION

PATENT NO. : 7,115,119 B2 Page 1 of 1
APPLICATION NO. : 10/441148
DATED : October 3, 2006
INVENTOR(S) : Desarzens et al.

It is certified that error appears in the above-identified patent and that said Letters Patent is hereby corrected as shown below:

On the front page, in the Inventor area, please add, after "Desarzens", --, André Lechot, Orvin (CH)--

In Col. 3, line 51, replace the two occurences of "recess" with --recesses--.

In Col. 3, line 55, replace the phrase "cross section 68" with --arm 13 of the--.

In Col. 5, line 4, replace the third "the" with --then--.

In Col. 5, line 10, replace the word "tug" with --along--.

In Col. 6, line 11, replace the word "he" with --the--.

Signed and Sealed this

Twenty-fifth Day of December, 2007

JON W. DUDAS
*Director of the United States Patent and Trademark Office*